US009452198B2

(12) United States Patent
Ribbeck et al.

(10) Patent No.: US 9,452,198 B2
(45) Date of Patent: Sep. 27, 2016

(54) LECTIN CONJUGATES FOR MUCIN HYDRATION

(71) Applicant: Massachusetts Institute of Technology, Cambridge, MA (US)

(72) Inventors: Katharina Ribbeck, Cambridge, MA (US); Thomas Crouzier, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/394,947

(22) PCT Filed: Mar. 15, 2013

(86) PCT No.: PCT/US2013/032442
§ 371 (c)(1),
(2) Date: Oct. 16, 2014

(87) PCT Pub. No.: WO2013/162771
PCT Pub. Date: Oct. 31, 2013

(65) Prior Publication Data
US 2015/0094255 A1    Apr. 2, 2015

Related U.S. Application Data

(60) Provisional application No. 61/637,017, filed on Apr. 23, 2012.

(51) Int. Cl.
A01N 37/18    (2006.01)
A61K 38/00    (2006.01)
A61P 31/00    (2006.01)
A61K 38/17    (2006.01)
A61K 47/48    (2006.01)

(52) U.S. Cl.
CPC ..... *A61K 38/1732* (2013.01); *A61K 47/48215* (2013.01)

(58) Field of Classification Search
CPC .................... A61K 47/48215; A61K 38/1732
See application file for complete search history.

(56) References Cited

U.S. PATENT DOCUMENTS

| 4,996,296 | A   |   | 2/1991  | Pecht et al.              |
|-----------|-----|---|---------|---------------------------|
| 5,284,934 | A   |   | 2/1994  | Allen, Jr.                |
| 7,687,608 | B2  | * | 3/2010  | Lancaster ...... A61K 38/25 |
|           |     |   |         | 424/124                   |
| 2003/0077317 | A1 |  | 4/2003  | Santos et al.             |
| 2004/0086499 | A1 |  | 5/2004  | Caldwell et al.           |
| 2005/0112188 | A1 | * | 5/2005  | Eliaz ......... A61K 9/0004 |
|           |     |   |         | 424/450                   |
| 2006/0058736 | A1 |  | 3/2006  | Alchas et al.             |
| 2008/0151180 | A1 |  | 6/2008  | Vanderbilt et al.         |
| 2008/0286211 | A1 |  | 11/2008 | Barker                    |
| 2015/0030661 | A1 |  | 1/2015  | Ribbeck et al.            |
| 2015/0051139 | A1 |  | 2/2015  | Lieleg et al.             |
| 2015/0094255 | A1 |  | 4/2015  | Ribbeck et al.            |
| 2015/0283208 | A1 |  | 10/2015 | Ribbeck et al.            |

FOREIGN PATENT DOCUMENTS

| JP | 02-191225 A     | 7/1990  |
|----|-----------------|---------|
| WO | WO 00/23023 A1  | 4/2000  |
| WO | WO 03/014078 A2 | 2/2003  |
| WO | WO 2007/132355 A2 | 11/2007 |
| WO | WO 2013/119668 A1 | 8/2013  |
| WO | WO 2013/119700 A1 | 8/2013  |
| WO | WO 2014/055127  | 4/2014  |

OTHER PUBLICATIONS

Gao et al. Lectin-conjugated PEG-PLA nanoparticles:Preparation and brain delivery after intranasal administration. Biomaterials. 2006. vol. 27, pp. 3482-3490.*
Gipson et al. Visualization of Conjunctival Goblet Cell Actin Cytoskeleton and Mucin Content in Tissue Whole Mounds. Exp Eye Res, 1997. vol. 65, pp. 407-415.*
Shinogi et al. Quantitative Analysis of Mucin and Lectin in Maxillary Sinus Fluids in Patients With Acute and Chronic Sinusitis. The Laryngospcope. 2001. vol. 111, pp. 240-251.*
Ogasawara et al. Sialic acid is an essential moiety of mucin as a hydroxyl radical scavenger. FEBS Letters, 2007. vol. 581, pp. 2473-2477.*
Liu et al. Nose-to-Brain Transport Pathways of Wheat Germ Agglutinin Conjugated PEG-PLA Nanoparticles. Pharm Res. 2012. Published online Dec. 4, 2011. vol. 29, pp. 546-558.*
Roberts et al. Chemistry for peptide and protein PEGylation. Advanced Drug Delivery Reviews, 2002. vol. 54, pp. 459-476.*
Andrews, G.P., et al., "Mucoadhesive Polymeric Platforms for Controlled Drug Delivery", European Journal of Pharmaceutics and Biopharmaceutics, 71: 505-518 (2009).
Cao, Y., et al., "Initiation of Glycogen Synthesis," Journal of Biological Chemistry, 268(29):21717-21721 (1993).
Caruso, F. et al., "Characterization of Polyelectrolyte-Protein Multilayer Films by Atomic Force Microscopy, Scanning Electron Microscopy, and Fourier Transfor Infrared Reflection-Absorption Spectroscopy", Langmuir, 14(16): 4559-4655 (1998).
Celli, J. et al., "Viscoclastic Properties and Dynamics of Porcine Gastric Mucin", Biomacromolecules, 6: 1329-1333 (2005).
Celli, J.P., et al., "Rheology of Gastric Mucin Exhibits a pH-Dependent Sol-Gel Transition", Biomacromolecules, 8(5): 1580-1586 (2007).
Cheetham, S., et al., "Binding Patterns of Human Norovirus-Like Particles to Buccal and Intestinal Tissues of Gnotobiotic Pigs in Relation to A/H Histo-Blood Group Antigen Expression", Journal of Virology, 81(7): 3535-3544 (2007).

(Continued)

*Primary Examiner* — Marcela M Cordero Garcia
(74) *Attorney, Agent, or Firm* — Hamilton, Brook, Smith & Reynolds, P.C.

(57) ABSTRACT

The invention provides, inter alia, conjugates of a hydratable polymer (such as PEG, polyethylene glycol) and a lectin (such as wheat germ agglutinin, WGA), compositions comprising these conjugates, as well as methods and targeted uses of these conjugates and compositions for, e.g., lubricating, maintaining hydration of, rehydrating, and/or inhibiting microorganism colonization of a biological surface in need thereof.

7 Claims, 9 Drawing Sheets

(56) References Cited

OTHER PUBLICATIONS

Critchfield, A., et al., "Permeability Properties of Cervical Mucus in Women at High Risk for Preterm Birth" 32nd Annual Meeting of the Society for Maternal-Fetal Medicin: The Pregnancy Meeting, Feb. 6-11, 2012, Dallas, Texas; Doppler Assessment, Fetus, Prematurity Poster Session III, 450 , 2 pages.

Crouzier, T., "Extreme pH and Salt Resistance of a Polysaccharide-based Multilayer Film by Mucin-lcctin Coupling." Poster #40 from Materials Processing Center Research Review Poster Session (Oct. 2011).

Crouzier, T., et al., "Mucin Multilayers Assembled through Sugar-Lectin Interactions," Biomacromolecules, 13: 3401-3408 (2012).

Dam, T. and Brewer, C.F., "Multivalent Lectin-Carbohydrate Interactions: Energetics and Mechanisms of Binding," Advances in Carbohydrate Chemistry and Biochemistry, 63:139-164 (2010).

de Repentigny, L., et al., "Characterization of Binding of *Candida albicans* to Small Intestinal Mucin and Its Role in Adherence to Mucosal Epithelial Cells," *Infection and Immunity*, 68(6):3172-3179 (2000).

Derrien, M., et al., "Mucin-Bacterial Interactions in the Human Oral Cavity and Digestive Tract," Gut Microbes, 1(4):254-268 (2010).

Fogelsen, S.J., "Treatment of Peptic Ulcer with Gastric Mucin," Experimental Biology and Medicine, 28:138 (1930).

Foster, S.N.E., et al., "Interaction of Polyacrylates with Porcine Pepsin and the Gastric Mucus Barrier: A Mechanism for Mucosal Protection", *Clinical Science*, 87:719-726 (1994).

Frenkel, E.S. and Ribbeck, K., "Salivary Mucins Protect Surfaces from Colonization by Cariogenic Bacteria," *Applied and Environmental Microbiology*, 81(1):332-338 (2015).

Gandhi, K.M., et al., "Binding of Virus-Like Particles of Norwalk Virus to Romaine Lettuce Veins", *Applied and Environmental Microbiology*, 76(24):7997-8003 (2010).

Gou, Y., et al., "Controlled Alternate Layer-by-Layer Assembly of Lectins and Glycopolymers Using QCM-D,"*ACS Macro. Lett.*, 1: 180-183 (2012).

Habte, H. H., et al., "Antiviral Activity of Purified Human Breast Milk Mucin," *Neonatology*, 92: 96-104 (2007).

Horisberger, M., "An Application of Ellipsometry: Assessment of Polysaccharide and Glycoprotein Interaction with Lectin at a Liquid/Solid Interface," *Biochimica et Biophysica Acta*, 632: 298-309 (1980).

Huang, L.C., et al., "In Vitro Activity of Human β-Defensin 2 Against *Pseudomonas aeruginosa* in the Presences of Tear Fluid," *Antimicrobial Agents and Chemotherapy*, 51(11):3853-3860 (2007).

Kohri, K, et al., "*Pseudomonas aeruginosa* Induces MUC5AC Production via Epidermal Growth Factor Receptor," *Eur Respir J*, 20:1263-1270 (2002).

Kristl, A. and Legen, I., "Mucous/Mucin Dispersions as a Model for Drug Absorption", *Farmacevtski Vestnik*, 50:270-271 (1999).

Legen, I. and Kristl, A., "Comparative Permeability of Some Acyclovir Derivatives Through Native Mucus and Crude Mucin Dispersions", *Drug Dev Ind Pharm*, 27(7): 669-674 (2001).

Lieleg, O., et al., "Characterization of Particle Translocation Through Mucin Hydrogels," *Biophysical Journal*, 98:1782-1789 (2010).

Lieleg, O., et al., "Mucin Biopolymers As Broad-Spectrum Antiviral Agents," *Biomacromolecules*, 13: 1724-1732 (2012).

Loyo, M., et al. "Quantitative Detection of Merkel Cell Virus in Human Tissues and Possible Mode of Transmission", International Journal of Cancer, 126:2991-2996 (2010).

Mahalingam, A., et al., "Inhibition of the transport of HIV in vitro using a pH-responsive synthetic mucin-like polymer system," *Biomaterials*, 32: 8343-8355 (2011).

Marshall, P., et al., "Localised mapping of water movement and hydration inside a developing bioadhesive bond," *Journal of Controlled. Release*; 95(3): 435-436 (Mar. 2004).

Neumann, G., et al., "Emergence and Pandemic Potential of Swine-Origin H1N1 Influenza Virus", Nature, 459(7249): 931-939 (2009).

Saladino, R., et al., "Efficacy of a Recombinant Endotoxin Neutralizing Protein in Rabbits with *Escherichia coli* Sepsis", *Circ. Shock*, 42(2):104-110 (1994).

Shi, L., et al., "Mucin Coating on Polymeric Material Surfaces to Suppress Bacterial Adhesion," *Colloids and Surfaces B: Biointerfaces*, 17:229-239 (2000).

Stern, G.A. and Zam, Z.S., "The Effect of Enzymatic Contact Lens Cleaning on Adherence of *Pseudomonas aeruginosa* to Soft Contact Lenses," *Ophthalmology*, 94:115-119 (1987).

Tian, P., et al., "Porcine Gastric Mucin Binds to Recombinant Norovirus Particles and Competitively Inhibits Their Binding to Histo-Blood Group Antigens and Caco-2 Cells", *Letters In Applied Microbiology*, 41:315-320 (2005).

Tian, P., et al., "Two-Log Increase in Sensitivity for Detection of Norovirus in Complex Samples by Concentration with Porcine Gastric Mucin Conjugated to Magnetic Beads", Applied and Environmental Microbiology, 74(14):4271-4276 (2008).

Tian, P., et al., "Specificity and Kinetics of Norovirus Binding to Magnetic Bead-Conjugated Histo-Blood Group Antigens", *Journal of Applied Microbiology*, 109:1753-1762 (2010).

Vladescu, I., et al., "An Adsorption Chromatography Assay to Probe Bulk Particle Transport Through Hydrogels", *Journal of Pharmaceutical Sciences*, 101(1):436-442 (2012).

Voinova, M.V. et al., "Visoelastic Acoustic Response of Layered Polymer Films At Fluid—Solid Interfaces: Continuum Mechanics Approach", Physica Scripta, 59: 391-412 (1999).

Weber, N. et al., "Formation of Viscoelastic Protein Layers on Polymeric Surfaces Relevant to Platelet Adhesion", *J Biomed Mater Res A*, 72(4): 420-427 (2005).

Wirth, M., et al., "Lectin-mediated Drug Delivery: Influence of Mucin on Cytoadhesion of Plant Lectins in vitro," *Journal of Controlled Release*, 79:183-191 (2002).

Yolken, R. H., et al., "Human Milk Mucin Inhibits Rotavirus Replication and Prevents Experimental Gastroenteritis," *J. Clin. Invest.*, 90: 1984-1991 (1992).

Yu, H., et al., "Interleukin-13 Induces Mucin 5AC Production Involving STAT6/SPDEF in Human Airway Epithelial Cells", Cell Communication & Adhesion , 17: 83-92 (2011).

Notification of Transmittal of the International Search Report and the Written Opinion for International Application No. PCT/US2013/032442; entitled, "Lectin Conjugates for Mucin Hydration ", Date of Mailing: Jun. 27, 2013.

Notification Concerning Transmittal of International Preliminary Report on Patentability for International Application No. PCT/US2013/032442, entitled, "Lectin Conjugates for Mucin Hydration", Date of Mailing: Nov. 6, 2014.

Notification of Transmittal of the International Search Report and the Written Opinion of the International Searching Authority for International Application No. PCT/US2013/024978, "Multilayer Films and Uses Thereof", Date of Mailing: May 8, 2013.

Notification Concerning Transmittal of International Preliminary Report on Patentability for International Application No. PCT/US2013/024978, titled: "Multilayer Films and Uses Thereof," Date of Mailing: Aug. 21, 2014.

Office Action for U.S. Appl. No. 14/376,714, Date of Mailing: Mar. 1, 2016.

Office Action for U.S. Appl. No. 14/376,714, entitled: "Multilayer Films and Uses Thereof," Date of Mailing: Sep. 16, 2015.

* cited by examiner

LECTIN CONJUGATES FOR MUCIN HYDRATION

RELATED APPLICATION

This application is the U.S. National Stage of International Application No. PCT/US2013/032442, filed Mar. 15, 2013, which designates the U.S., published in English, and claims the benefit of U.S. Provisional Application No. 61/637,017, filed on Apr. 23, 2012.

The entire teachings of the above applications are incorporated herein by reference.

BACKGROUND OF THE INVENTION

With aging, the mucus layer tends to dehydrate, which leads to discomfort and increased risk of infections. Aging is believed to result in a deficit in the quantity or quality of mucin production, which in turn causes dehydration of the mucus layer. Accordingly, a need exists for solutions to overcome this dehydration.

A further need exists for including compositions that treat these dehydrations into commonly used hygiene products to restore hydration of, for example, the mucus in the eyes, mouth, female genital tract, lungs, or the digestive tract.

SUMMARY OF THE INVENTION

The invention provides compositions for treating, inter alia, dehydration of mucus layers. In a first aspect, the invention provides an isolated conjugate of a hydratable polymer and a lectin. In some embodiments, the hydratable polymer is hydrated. In certain embodiments, the hydratable polymer is a polyether, such as polyethylene glycol (PEG), which, in more particular embodiments, has an average molecular weight of about, at least, or up to 10, 20, 30, 40, 50, 60, 70 or 80 Kda; more particularly, where the PEG has an average molecular weight of about 25-55 Kda; and still more particularly where the PEG has an average molecular weight of about 35-45 Kda.

In certain embodiments the lectin in the conjugate comprises a fragment of wheat germ agglutinin (WGA), e.g., comprises an amino acid sequence at least 80% identical to a 30-50 amino acid fragment of SEQ ID NO: 1.

In a particular embodiment, the invention provides a synthetic conjugate of hydrated polyethylene glycol (PEG) having an average molecular weight of about 35-45 Kda and a mucin-binding fragment of a lectin, and in some particular embodiments, the lectin is wheat germ agglutinin (WGA). In some embodiments, the PEG is linear.

In another aspect, the invention provides compositions comprising any of the foregoing conjugates and, in particular embodiments, aqueous solutions. The compositions provided by the invention can further comprise glycerin, xanthan gum, propylene glycol, sorbitol, polysorbate, hydroxyethylcellulose, or a combination thereof and may optionally include one or more suitable additional active ingredients.

In a further aspect, the invention provides methods of lubricating, maintaining hydration of, rehydrating, and/or inhibiting microorganism colonization of a biological surface in need thereof comprising contacting the surface with an effective amount of any of the conjugates and compositions provided by the invention. In particular embodiments, the method comprises maintaining hydration of or rehydrating a mucosal surface in a mammal; preferably wherein the mammal is a human, and in particular embodiments, the mucosal surface is the mucosa of the eyes, mouth, nose, female genital tract, the respiratory tract, or digestive tract. In other embodiments, the methods comprise lubricating an articular joint surface.

BRIEF DESCRIPTION OF THE DRAWINGS

The foregoing will be apparent from the following more particular description of example embodiments of the invention, as illustrated in the accompanying drawings. The drawings are not necessarily to scale, emphasis instead being placed upon illustrating embodiments of the present invention.

FIG. 3A shows the hydrated thickness of a WGA lectin coating or a (WGA-PEG) conjugate coating. FIG. 3B shows the calculated hydration (% of mass composed of water) for both coatings.

FIG. 4A is a graphical summary of the evolution of hydrated thickness of mucin (PGM) when coated on a surface. This adsorption is followed by the addition of WGA or (WGA-PEG) around t=3900 seconds. FIG. 4B is a bar graph of the resulting hydration (% of mass composed of water).

DETAILED DESCRIPTION OF THE INVENTION

Figure 1:
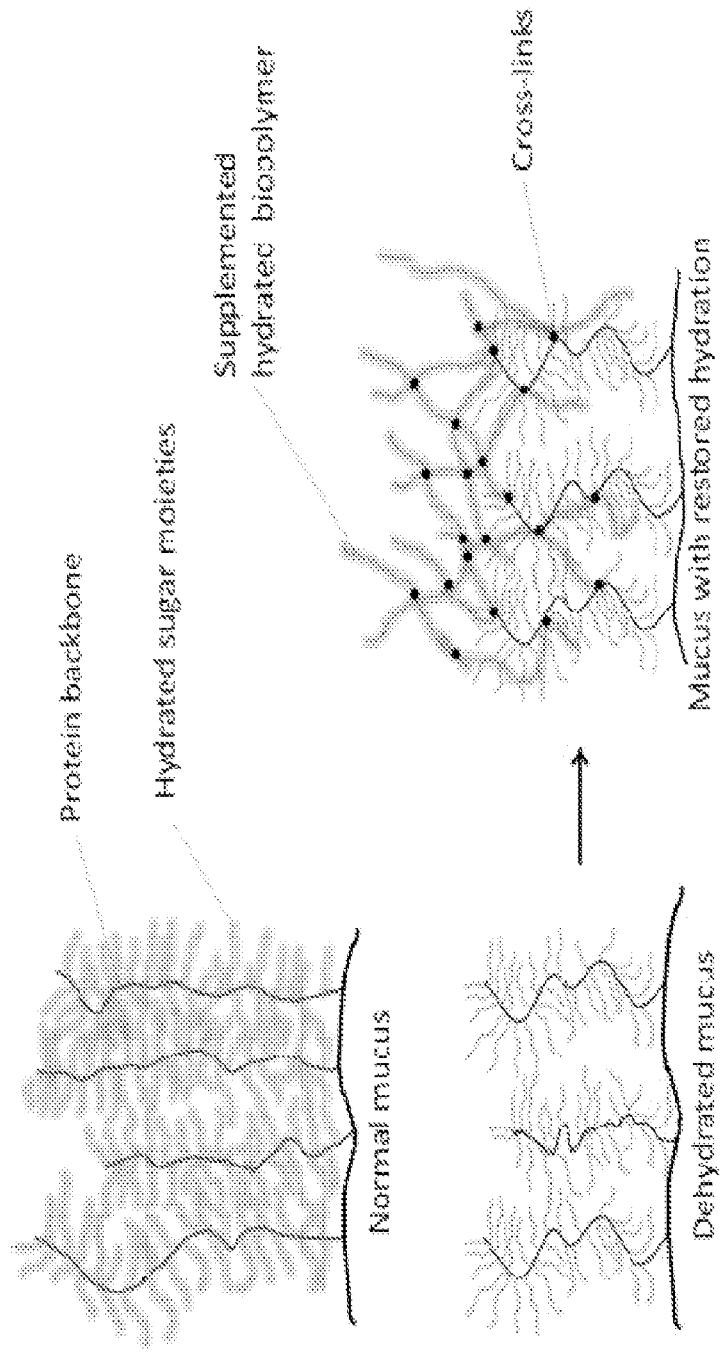
FIG. 1. provides a model of how to treat dehydration of the mucus layer in accordance with the present invention. The dehydrated mucus layer is supplemented by highly hydrated polymers that bind to the mucin polymers via lectins for example. These polymers can be included in commonly used hygiene products to be delivered to the mucosa of the eyes, mouth, female genital tract, or the respiratory and digestive tracts.

A description of example embodiments of the invention follows.

The invention provides, inter alia, conjugates of a hydratable polymer and a lectin, compositions containing these conjugates, and methods of using these conjugates and compositions. These conjugates will be referred to as "conjugates provided by the invention," "conjugates of the invention," and the like, and compositions containing the conjugates provided by the invention are "compositions provided by the invention," "compositions of the invention" and the like and, for brevity, the application references "conjugates and compositions provided by the invention" or "conjugates and compositions of the invention" to encompass both the conjugates provided by the invention and compositions provided by the invention.

"Hydrateable polymer" refers to a high molecular weight (greater than about 1 Kda) polymer capable of retaining a large relative volume of aqueous solution. Hydratable polymers can be polysaccharides, dextrans, hyaluronic acids, alginates, and synthetic polymers that mimic the properties of these compounds, as well as mixtures of any of these hydratable polymers. The hydratable polymer may be branched or linear or a mixture of branched and linear polymers, e.g., about 1, 2, 3, 4, 5, 10, 15, 20, 30, 40, 50, 60, 70, 80, 90, 95, 96, 97, 98, 99, or 100% (w/w) linear versus branched. The hydratable polymers may have various amounts of cross-linking, e.g., 0, 1, 2, 3, 4, 5, 10, 15, 20, 30, 40, 50%, or more cross-linking. In particular embodiments, the hydratable polymer is a polyether, such as polyethylene glycol (PEG). The PEG, in some embodiments, has an average molecular weight of about, at least, or up to about 10, 20, 30, 40, 50, 60, 70 or 80 Kda, or more. In more particular embodiments, the PEG has an average molecular weight of about 25-55 Kda and in more particular embodiments, the PEG has an average molecular weight of about 35-45 Kda. The PEG, in particular embodiments, is mostly linear (e.g., at least 50, 60, 70, 80, 90, 95, 96, 97, 98, 99% (w/w) or more linear).

"Lectin," and the like, refers to physiologically compatible protein domains that bind to a sugar moiety associated with a glycosylated polymer. Exemplary lectins for use in the invention include a fragment of wheat germ agglutinin (WGA) lectin (for example, as sold by Vector Laboratories under Catalog No. L-1020) as well as a fragment of the WGA provided in UniprotID P10969 ("P10969"), incorporated by reference in its entirety, (see also GenBank accession no: AAA34257, incorporated by reference, including reference annotations), as well as Jacalin lectin (GenBank accession nos: AAA32680-AAA32677, incorporated by reference) or *Sambucus nigra* lectin (GenBank accession nos: AAL04122-AAL04119, AAC15885, AAN86132, and AAN86131, incorporated by reference). In particular embodiments, the lectin comprises an amino acid sequence that is at least 60, 65, 70, 75, 80, 85, 90, 95, 96, 97, 98, 99, or 100% identical to any of the foregoing, (including, in particular embodiments, P10969 or SEQ ID NO: 1) or a functional fragment thereof, such as a contiguous fragment of 30, 40, 50, 60, 70, 80, 90, 100, 120, 140, 160, or 180 amino acids, or more of any of the foregoing, e.g., comprising a 30-50 amino acid fragment at least 80% identical to a lectin domain such as a ChtBD1 (PSSM ID: 211512) domain, as exemplified by, for example, any one of the regions defined by amino acids 45-81, 88-124, or 132-167 of P10969 or SEQ ID NO: 1, e.g., comprising at least 1, 2, or all 3 of these domains, or higher-order numbers of lectin domains, e.g., polypeptides comprising 1, 2, 3, 4, 5, 6, 7, 8, 9, 10, or more lectin domains.

By way of example, wheat germ agglutinin (WGA) is a 36,000 molecular weight protein consisting of two identical subunits. WGA contains a group of closely related isolectins, with an isoelectric point about pH 9. The receptor sugar for WGA is N-acetylglucosamine, with preferential binding to dimers and trimers of this sugar. WGA can bind oligosaccharides containing terminal N-acetylglucosamine or chitobiose, structures which are common to many serum and membrane glycoproteins. Bacterial cell wall peptidoglycans, chitin, cartilage glycosaminoglycans and glycolipids can also bind WGA. Native WGA has also been reported to interact with some glycoproteins via sialic acid residues (see succinylated WGA). This lectin has proven useful for the purification of insulin receptors and for neuronal tracing.

Additional molecules that can perform the function of a lectin include antibodies that specifically bind to a mucin that, when the antibody binds to a sugar moiety associated with a mucin, is a lectin according to the invention. "Antibody" refers to both whole immunoglobulins as well as antigen (i.e. mucin)-binding fragments of immunoglobulins that contain an antigen-binding domain comprising at least 3, 4, 5, or 6 complementary determining regions (CDRs). Antibodies can be from any source including human, orangutan, mouse, rat, goat, sheep, rabbit and chicken antibodies, as well as synthetic, engineered antibodies. Antibodies may be polyclonal, monoclonal, monospecific, polyspecific, non-specific, humanized, camelized, single-chain, chimeric, synthetic, recombinant, hybrid, mutated, and CDR-grafted antibodies. Small molecules can, in some embodiments of the invention, function as lectins. For example, thiol groups can link the hydratable polymer to a mucin as can highly positively charged chemical groups.

Lectins for use in the compositions and conjugates provided by the invention can be recombinantly produced, chemically synthesized, or isolated from natural sources.

"Mucin" and the like is a highly glycosylated protein capable of forming gels, generally comprising an amino and/or carboxy regions that are cysteine-rich and a central region enriched for serine and/or threonine residues and associated O-linked and/or N-linked oligosaccharides. Exemplary mucins include, for example, the human mucins, MUC1 (human GeneID No. 4582), MUC2 (human GeneID No. 4583), MUC5AC (human GeneID No. 4586), and MUC5B (human GeneID No. 727897). Additional mucin sequences include MUC5AC mucin (see, e.g. UniGene IDs 3881294, 1370646, 1774723, 1133368 and HomoloGene 130646), a MUC5B (see, e.g., HomoloGene 124413), a MUC6 (see, e.g., HomoloGene 18768), MUC2 (see, e.g., HomoloGene 130504, 131905, 132025, or 133451), as well as porcine MUC5AC (see, e.g., UnigeneIDs 441382, 5878683; GeneID No. 100170143, and reference sequences AAC48526, AAD19833, and AAD19832). Other mucins include bovine submaxillary mucin (BSM, also known as MUC19; see e.g. GeneID No. 100140959; see HomoloGeneID 130967; see reference protein sequence XP_003586112.1).

The conjugates provided by the invention can be made by coupling the hydratable polymer and lectin (or suitable substitute molecule) by any suitable means. For example, the hydratable polymer and lectin can be coupled by ester, amide, thiol, ether, or phosphodiester linkages, as well as by nucleic acid hybridization, e.g. by hybridizing complementary nucleic acids (including both naturally occurring nucleic acids, such as DNA and RNA as well as synthetic nucleic acid) coupled to the hydratable polymer and lectin. In particular embodiments, the hydratable polymer and lectin can be coupled by amide linkage. The hydratable polymer and lectin can be conjugated, by any means, in a stoichiometric ratio (w/w) of about 100:1, 50:1, 25:1, 10:1, 5:1, 2:1, 1:1, 0.5:1, 0.25:1, 0.10:1, 0.05:1, or 0.01:1. In particular embodiments the hydratable polymer and lectin are conjugated in a stoichiometric ratio of about between 50:1 and 1:1, e.g., between about 25:1 to 2:1, or between about 25:1 to 5:1, or about 10:1, e.g. about 10:1 PEG:WGA. The resulting conjugate can, in certain embodiments, be a mixture of different ratios of hydratable polymer and lectin.

The conjugates provided by the invention may be mixed in an aqueous solution at a concentration of about 0.125, 0.20% (w/v), 0.25% (w/v), 0.30% (w/v), 0.35% (w/v), 0.40% (w/v), 0.45% (w/v), 0.50% (w/v), 0.55% (w/v), 0.6% (w/v), 0.65% (w/v), 0.7% (w/v), 0.75% (w/v), 0.8% (w/v), 0.85% (w/v), 0.9% (w/v), 0.95% (w/v), 1% (w/v), 1.5% (w/v), 2.0% (w/v), 2.5% (w/v), 3.0% (w/v), 3.5% (w/v), 4.0% (w/v), or 4.5% (w/v) or more, when hydrated. In more particular embodiments, the concentration is between about 0.125 to about 2.0% (w/v), e.g. between about 0.2 to about 1.2% (w/v), or more particularly about 0.25 to about 1.0% (w/v)

The conjugates provided by the invention may be mixed in an aqueous solution with a salt concentration of about 20 nM, 40 mM, 60 mM, 80 mM, 100 mM, 120 mM, 140 mM, 160 mM, 180 mM, 200 mM, 220 mM, 240 mM, 260 mM, 280 mM, 300 mM, 320 mM, 340 mM, 360 mM, 380 mM, 400 mM, 420 mM, 440 mM, 460 mM, 480 mM, 500 mM, 520 mM, 540 mM, 560 mM, 580 mM or 600 mM for a 1:1 electrolyte salt when hydrated, or an approximate (e.g., within about 2, 4, 5, 6, 8, 10, 12, 14, 15, 16, 18, 20, 25, or 30%), equivalent ionic strength. In more particular embodiments the salt concentration is about 20 to about 500 mM, e.g., about 150 to about 300 mM; or in other embodiments about 200 to about 500 mM.

The conjugates provided by the invention can be incorporated with mucin/lectin multilayer films as described in Internation Patent Application No. PCT/US2013/024978, filed Feb. 6, 2013, which is incorporated by reference in its entirety.

In some embodiments, the conjugates and composition provided by the invention can be detectably labeled. For example, they may be fluorescently labeled, dye labeled, radiolabeled, biotinylated, et cetera. Because of their biocompatibility, detectably labeled conjugates and composition provided by the invention can be used in method of visualizing a substrate, such as a biological substrate, such as a sugar-containing molecule.

The conjugates and compositions provided by the invention can be used in a variety of methods. For example, methods of lubricating, maintaining hydration of, rehydrating, and/or inhibiting microorganism (including bacteria, viruses, fungi, Achaea, et cetera) colonization of or diffusion on a biological surface in need thereof comprise contacting the biological surface with an effective amount of the conjugates and compositions provided by the invention. Biological surfaces to be treated by these methods are typically, although not necessarily, in a subject, particularly a mammalian subject, including, in particular embodiments, a human subject. In particular embodiments, the subject to be treated by the methods provided by the invention is human and can be male or female and may be at any stage of development: e.g., prenatal, neonatal, infant, toddler, grade-school-age, teenage, early adult, middle-age, or geriatric, e.g., at least or about 1, 2, 3, 4, 5, 6, 7, 8, 9, 10, 15, 18, 20, 21, 25, 30, 35, 40, 45, 50, 55, 60, 65, 70, 75, 80, 85, 90, 95, 100, 105 years old, or more. Particular biological surfaces to be treated by the methods of the invention include joints, such as articular joints, as well as mucosa, including mucosa of the eyes, mouth, nose, the urogenital genital tract (such as the female genital tract), the respiratory tract, or digestive tract, as well as combinations of these.

Any suitable delivery mode known to the skilled artisan is appropriate for delivering the conjugates and compositions provided by the invention. Exemplary delivery modes include topical solutions, gels, lotions, creams, ointments, or pastes; other modalities includes oral administration, e.g., for stomach or intestinal delivery; enemas; or injection. For example, the conjugates and compositions provided by the invention can, in some embodiments, be incorporated in hygiene products, lotions, aqueous solutions (e.g., eye drops), gels; to affect saliva, in some embodiments, they can be provided in toothpaste; for embodiments to treat stomach mucosa, edible forms, such as yogurt, can be used.

Thus, the invention is also directed to a composition, such as a pharmaceutical composition, comprising one or more of the conjugates provided by the invention. For instance, the compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, et cetera.

Methods of introduction of these compositions include, but are not limited to, intradermal, intramuscular, intraperitoneal, intraocular, intravenous, subcutaneous, topical, oral and intranasal. The pharmaceutical compositions of this invention can also be administered as part of a combinatorial therapy with other compounds.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, that notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the compounds can be separated, mixed together in any combination, present in a single vial or tablet. Compounds assembled in a blister pack or other dispensing means is preferred. For the purpose of this invention, unit dosage is intended to mean a dosage that is dependent on the individual pharmacodynamics of each compound and administered in FDA approved dosages in standard time courses.

The conjugates and compositions provided by the invention can be used in additional applications, such as personal hygiene products (e.g., mouth wash, toothpaste, soaps, lubricants (including personal lubricants)), foods (e.g., baby formula, gum, yogurt), wound care products (e.g., ointments, bandages) or lubricants to support our immune system. Additional applications include applying the conjugates and compositions provided by the invention to human work surfaces, such as doorknobs, table tops, faucet handles, toilets, phones, et cetera. The protective effects of the conjugates and compositions provided by the invention can also be useful in filtration applications, such as, for example, ductwork, and filters for ductwork, e.g., in environment control systems such as heating and air conditioning, e.g. enclosed spaces, such as in automobiles, trains, airplanes, subways, et cetera.

EXAMPLES

Forcing a very hydrated polymer to strongly interact with the mucin is not trivial since most hydrated polymers are repulsed by mucin. To overcome this repulsion we prepared conjugates of the Wheat Germ agglutinin lectin protein (WGA) and Polyethylene Glycol (PEG). The WGA lectin is a globular protein that binds strongly to the mucin sugars and the PEG (Polyethylene glycol) is a very hydrated polymer.

Figure 2:
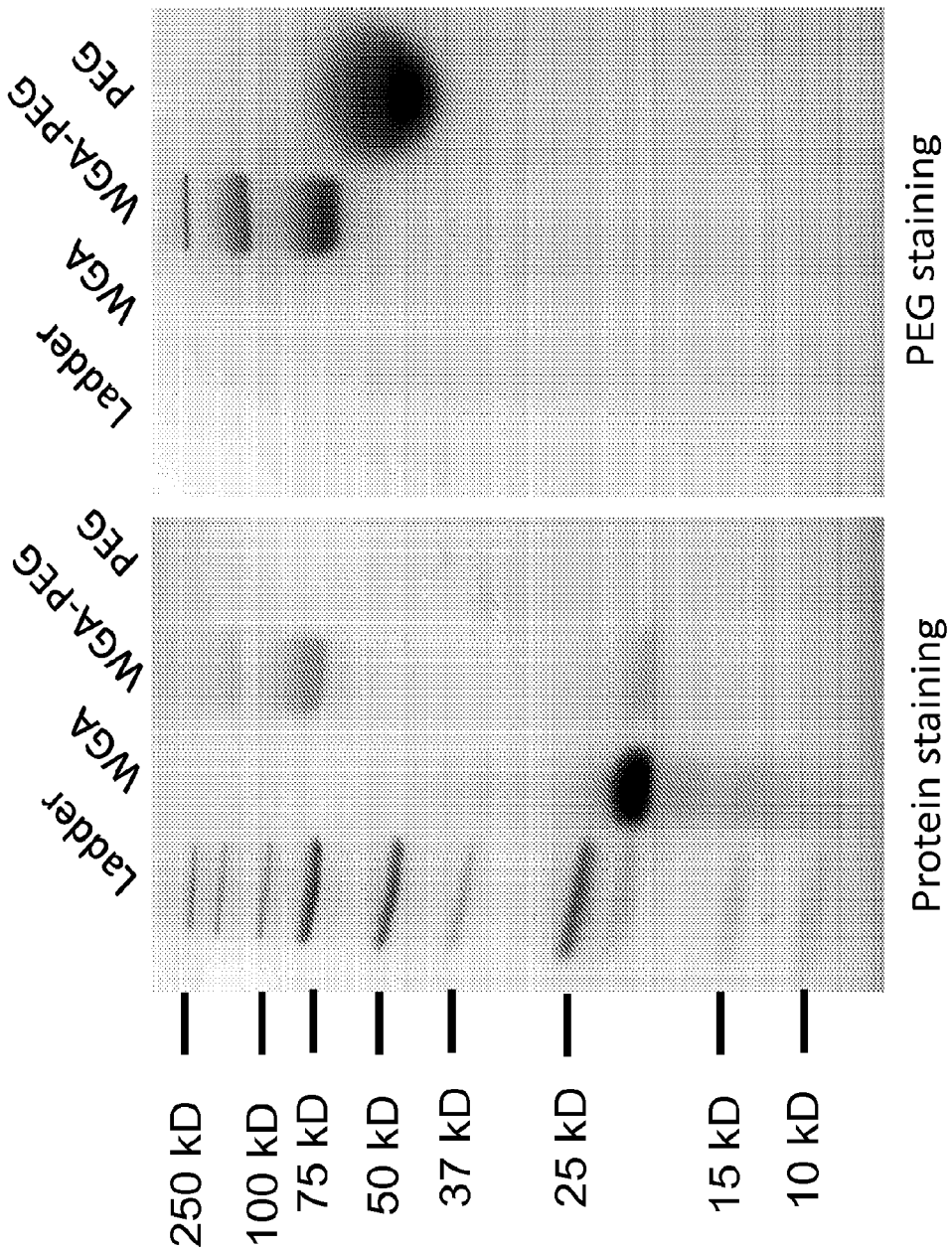
FIG. 2. shows a micrograph of SDS-PAGE gels of the WGA, PEG and the WGA-PEG conjugate. The left gel shows the protein staining showing that several WGA-PEG conjugate populations are generated. The right gel shows how the PEG staining confirms that these populations contain PEG.

The WGA was obtained from Vector Laboratories (Ref: L-1020) and was reacted with PEG (40 Kda) and purified by centrifugation filtering and size exclusion chromatography (SEC). A micrograph of SDS-PAGE gels of the WGA, PEG and the WGA-PEG conjugate is shown in FIG. 2. PEG was covalently grafted to WGA by using Methoxy PEG Succinimidyl Carboxymethyl Ester that reacted with the amine groups on WGA and formed amide bonds.

Figures 3A, 3B:
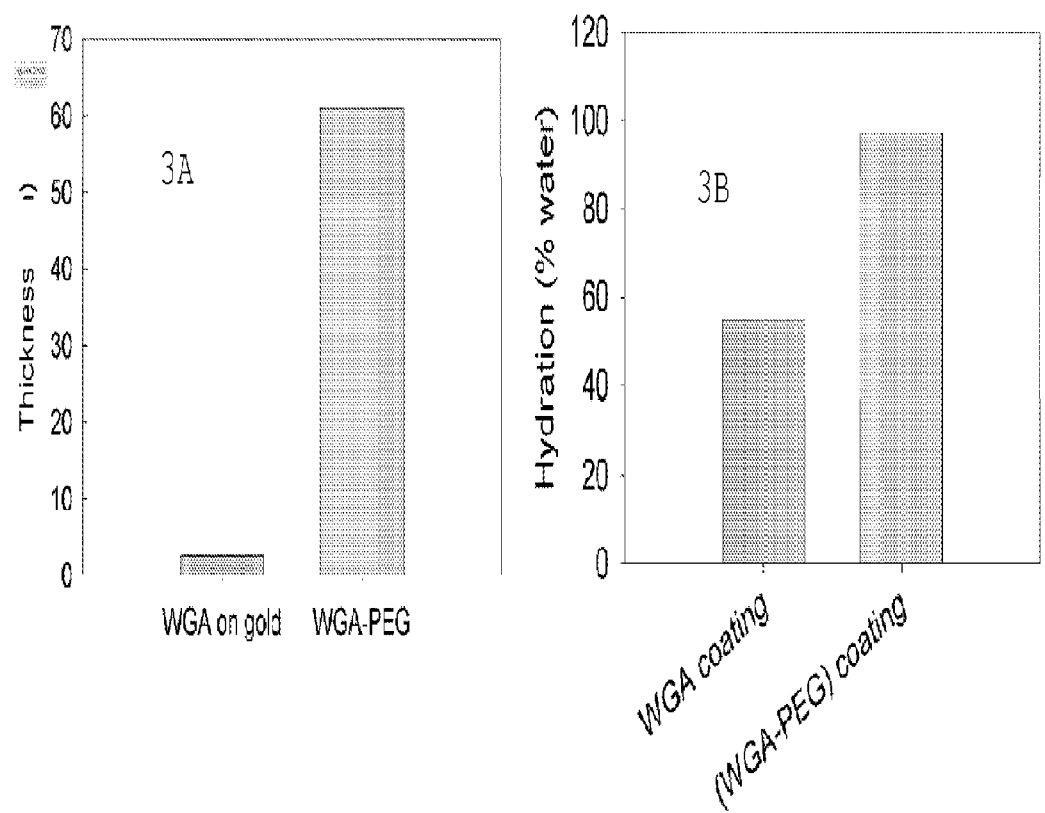
FIGS. 3A-3B summarize studies on the effect of WGA alone or (WGA-PEG) on surface thickness and hydration.

For further analysis, the (WGA-PEG) conjugate was then adsorbed on a surface. The hydrated thicknesses as well as the water content of the coatings formed were measured by a combination of Quartz Crystal Microbalance with Dissipation measurement and spectrometric ellipsometry, which are shown in FIG. 3. Coatings of (WGA-PEG) were very thick and hydrated coating compared to WGA. This confirmed that the water binding capacity of PEG was maintained when conjugated to WGA.

Next we verified that (WGA-PEG) could bind mucin, and looked for any change in the hydration of the mucin. The surface was first coated with mucin (PGM), then WGA or (WGA-PEG) was added. The results are summarized in FIG. 4.

Figures 4A, 4B:
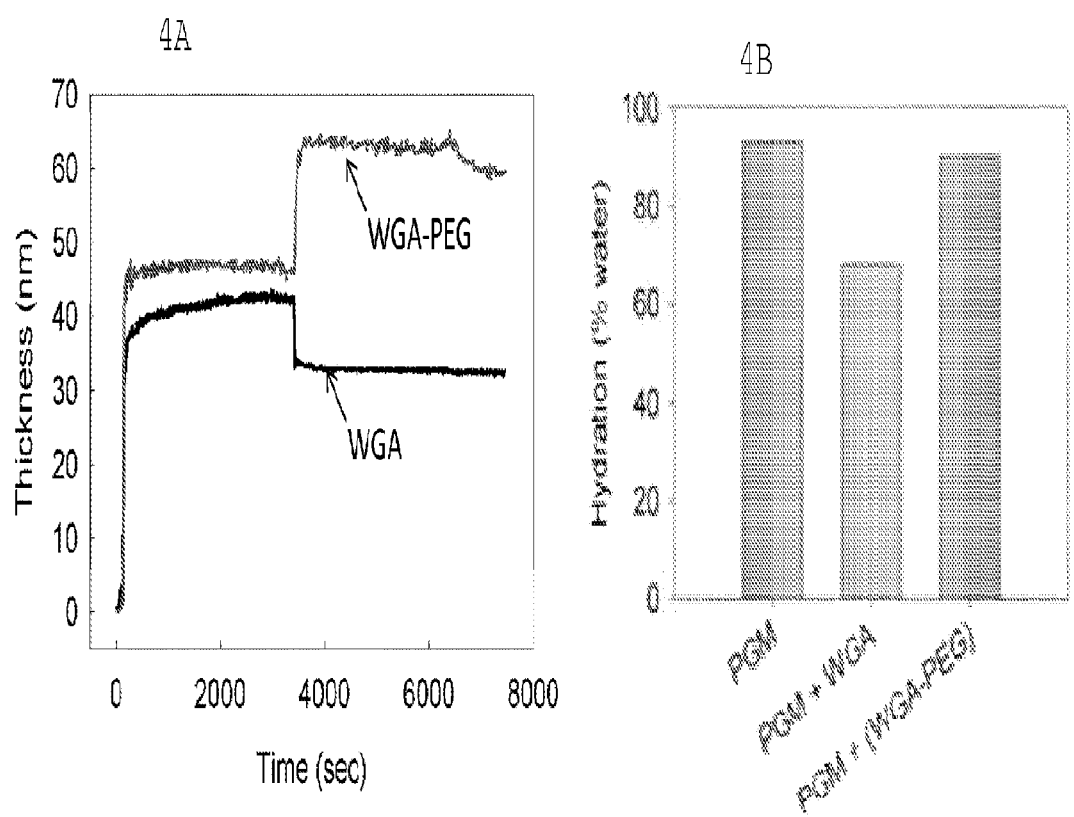
FIGS. 4A-4B summarize measurements on the surface thickness over time and hydration of WGA alone or (WGA-PEG) when binding to mucin.

When WGA was added to mucin, the mucin coating collapsed and released water (FIG. 4A). Consequently, the hydration decreased from ~90% to ~70% (FIG. 4B). When (WGA-PEG) was added instead of WGA, the hydrated thickness increased (FIG. 4A) and the hydration stayed at ~90% (FIG. 4B). In sum, (WGA-PEG) bound well to mucin and (Mucin-PEG) brought hydration to the mucin layer.

Figures 5A, 5B:
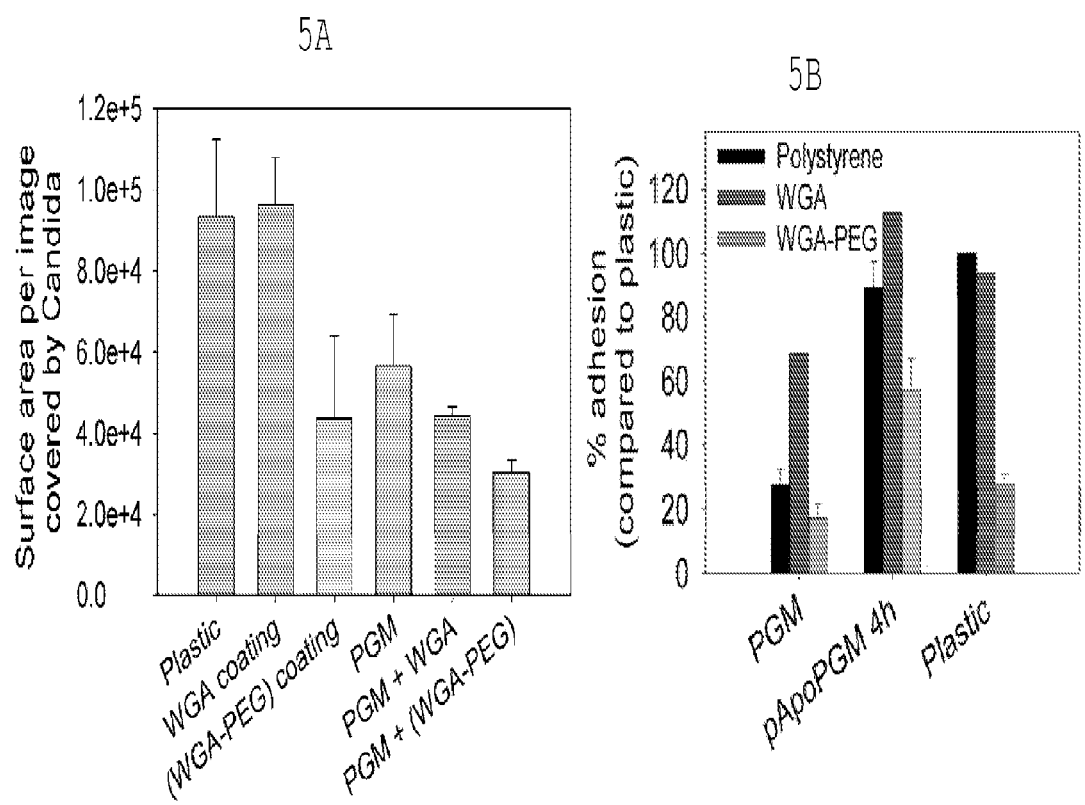
FIGS. 5A-5B illustrate the pathogen-repellent properties of WGA-PEG. 5A is a bar graph illustrating the surface area coverage of the yeast *Candida albicans* on various surfaces. "PGM" is mucin, specifically porcine gastric mucin. 5B shows similar results for GFP-expressing *Escherichia coli* bacteria. The addition of WGA-PEG reduces adhesion of the bacteria. However, WGA alone increased binding of *E. coli*.

Next, we investigated whether mucin's functionalities (hydration, lubrication, resistance to microorganisms colonization) were maintained once modified by (WGA-PEG). To this end, we looked at yeast interaction with mucin, and mucin modified with (WGA-PEG). GFP-expressing yeast (*Candida albicans*) were deposited on (WGA-PEG) coatings or mucin coating and mucin coatings with (WGA-PEG). The binding of the yeast was then measured and the results are summarized in FIG. 5A. In sum, (WGA-PEG) coatings were as efficient as repelling *candida* as mucin (PGM) coatings and (WGA-PEG) functionalization of mucin (PGM) coatings did not reduce their capacity to repel the yeast and actually increased this property. 5B shows similar results for GFP-expressing *Escherichia coli* bacteria.

Additional data generated are shown in FIGS. 6-9.
Results and Discussion:
WGA-PEG Synthesis Results in High Molecular Weight Conjugates.

In this work we focused on restoring two essential properties of mucus: its high hydration and its ability form an effective barrier against pathogens. We hypothesized that the hydration and antifouling properties of PEG can be transferred to biological surfaces. To maximize the interaction between PEG and the mucosa, a lectin carbohydrate-binding protein was conjugated to PEG chains (FIG. 1). The wheat germ agglutinin lectin (WGA) used here binds N-acetylglucosamine residues, which are present in abundance in both mucins and on the surface of cells. The conjugate is synthesized using an amine-reactive derivative of 40 kD PEG, then purified by size exclusion. The product was analyzed by SDS-PAGE, with protein and PEG staining shown in FIG. 2. As expected, WGA monomers are located around 18 kD and free PEG is found around 40 kDa. The protein stain reveals that the conjugation products are of high molecular weigh with estimated molecular weighs around 90 kD, 130 kD and 170 kD which could correspond to 1, 2 and 3 PEG per WGA monomer. In addition, the iodine staining confirms that these products are indeed pegylated.

WGA-PEG can Bind Mucin and Cell Surface In Vitro and In Vivo

Figures 6A, 6B, 6C:
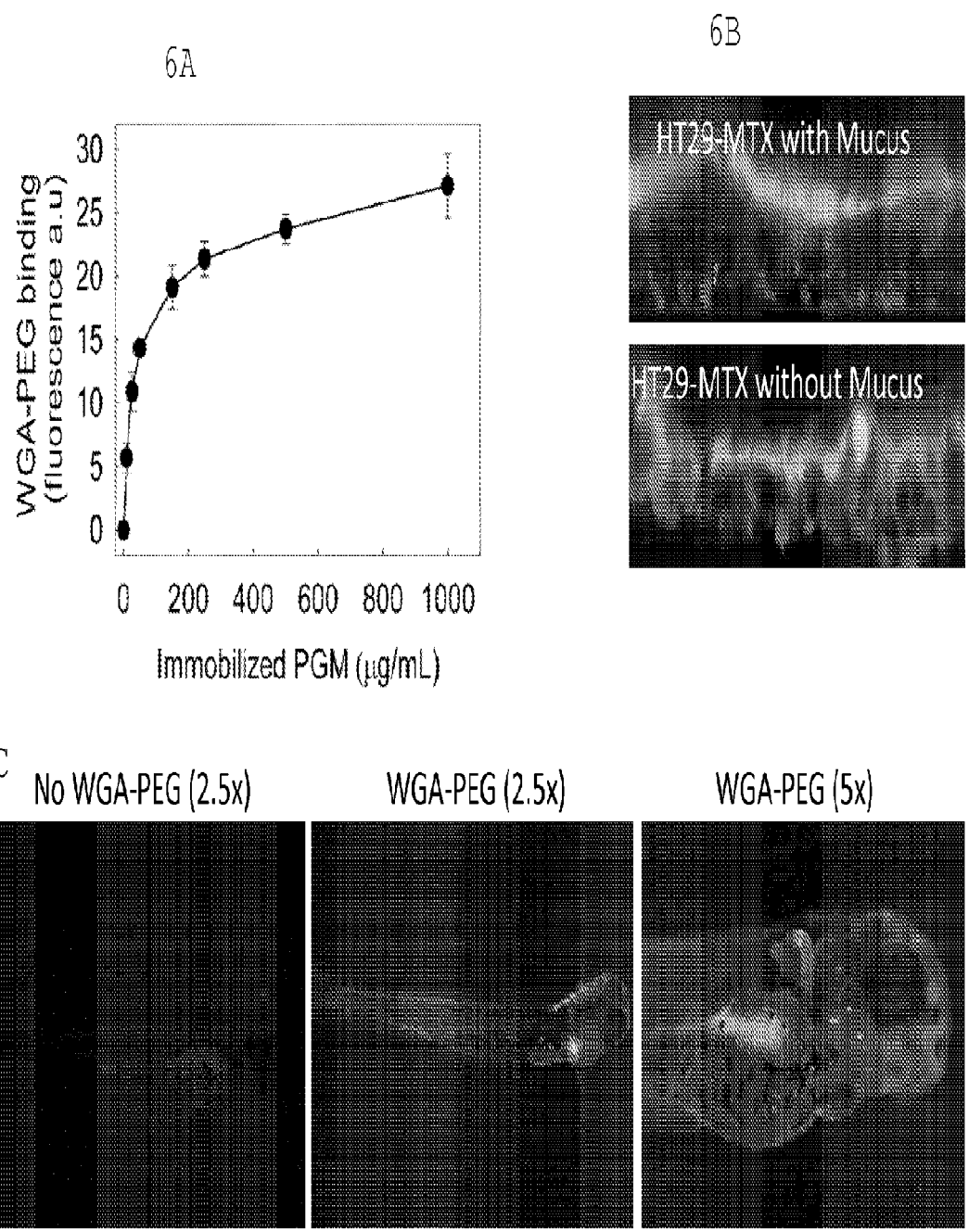
FIGS. 6A-6C show the capacity of WGA-PEG to bind biological molecules and surfaces. The conjugates binds surface-immobilized mucins, cell surfaces of a mucus-producing epithelial cell model (HT29-MTX) and covers a large area of zebra fish embryos. 6A shows the ability of WGA-PEG to bind surface-immobilized mucins (Pig Gastric Mucins, PGM). The binding is detected by measuring the fluorescence of fluorescently labeled WGA-PEG, where fluorescein is covalently linked to WGA. The binding of WGA-PEG is increased with the increase of immobilized PGM. 6B shows the ability of WGA to cover the surface of HT29-MTX mucus-producing cell line. Fluorescently labeled WGA-PEG (in green), cover the surface of HT29-MTX. WGA-PEG was able to bind to the cell surface both when mucus was present and after the cells were treated with the mucolytic agent: N-acetylcysteine (NAC). 6C Shows the labeling of a whole organism (zebra fish embryo, 100 hours post fertilization) with the WGA-PEG. Control shows no or little fluorescence. The two other images shows that WGA- PEG is covering the whole fish and lighting up single cells, corresponding to the mucus-secreting goblet cells.

The conjugation of high molecular weight polymers to proteins can jeopardize their bioactivity by altering the protein's surface chemistry and preventing steric access to substrates. In our case, attaching one or more 40 kD PEG chains to the lectin could hinder the lectin's ability to bind sugar residues. We thus tested the ability of the WGA-PEG conjugate to bind to mucin or cell-surface bound glycan in vitro and in vivo. FIG. 6A shows that binding of fluorescently labeled WGA-PEG increases with increased amount of immobilized PGM, confirming that at least a fraction of the conjugate has retained its ability to bind sugar residues present on mucins. Since the molecules is to be using on the mucosa, binding of the conjugate was also test on an epithelial cells lines able to produce mucus. FIG. 6B show confocal microscopy cross-section with WGA-PEG binding to the mucus layer (in green; top) on the top of the cells (in red; bottom). Removal of the mucus using a mucolytic agent shows that the conjugate can also bind cell surface. The ability of the conjugate to bind biological surface was further confirmed in an in vivo zebrafish model, exposed with WGA-PEG for an hour. As shown in FIG. 6C, the fish were stained both on the surface and in internal organs. In particular, mucus producing goblet cells were strongly stained.

Highly Hydrated Mucin Coatings can be Dehydrated by Deglycosylation

With confidence that the conjugate can bind the mucosa, we test if this conjugate can reconstitute some of the properties of the mucus layer covering our epithelium. We first focused on the ability of the WGA-PEG molecule to mimic mucin's ability to retain water to the surfaces. Hydration of adsorbed layers of polymer or proteins can be measured on synthetic surfaces by using quartz crystal microbalance with dissipation and ellipsometry that respectively measure hydrated mass and dehydrated mass (see FIG. 4A). The fraction of water in the adsorbed mass (i.e hydration) can then be extracted from these two pieces of information. Mucins form highly hydrated coatings with ~95% of the monolayer's mass being water. So called apo-mucins" were generated by removing the glycans from mucin's protein core. This led to a dehydration of the adsorbed protein layer. W found that by increasing the extent of deglycosylation, we could decrease the hydration of the resulting mucin layers (FIG. 4B). These results show that mucin's glycosylation is at least partially responsible for the high hydration of mucins. An intermediate extent of deglycosylation reduced hydration, from 95% to ~35% for while maintaining some WGA binding sites. This condition was chosen to serve as a model for dehydrated mucins.

WGA-PEG can Restore Hydration of Deglycosylated Mucins

Figure 7:
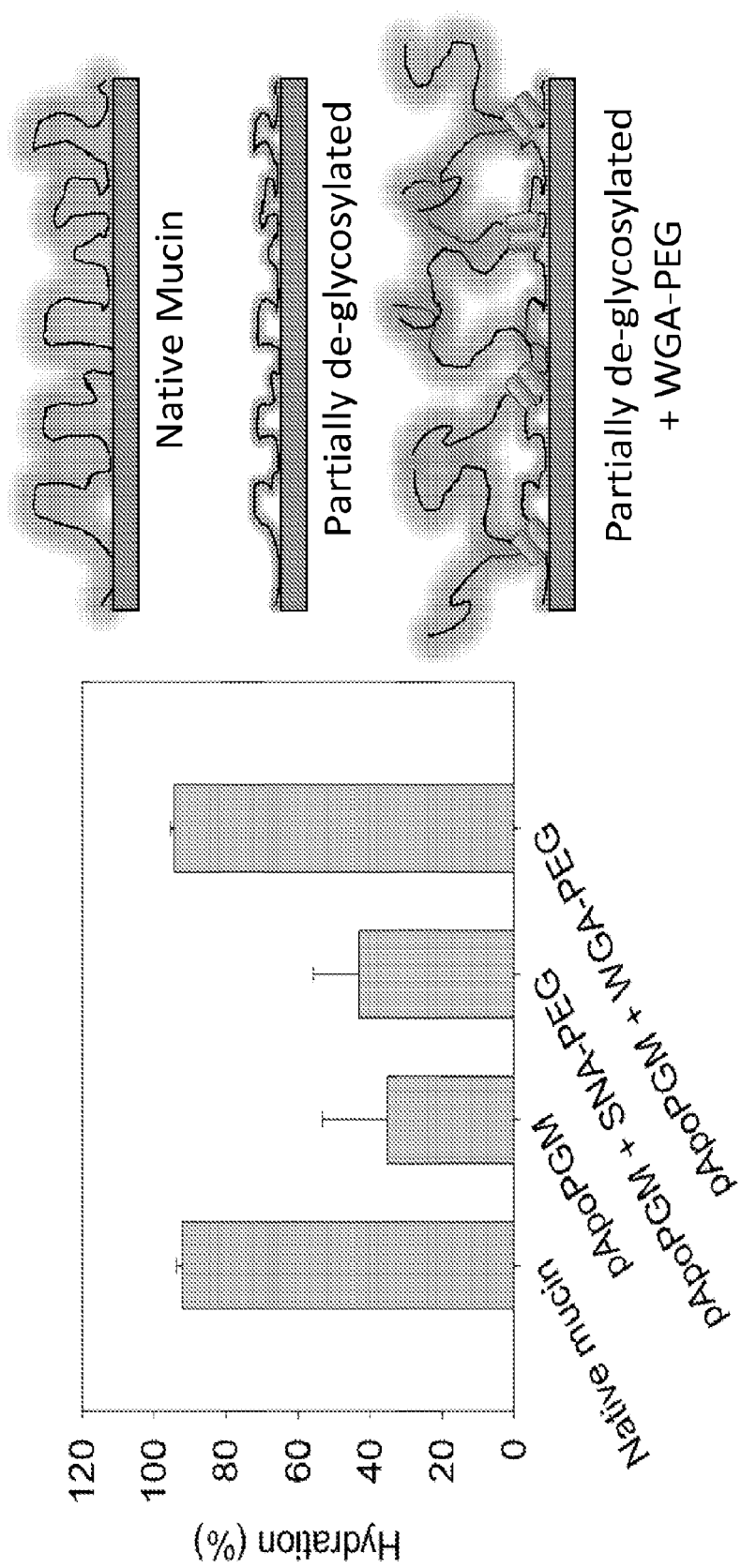
FIG. 7 shows the capacity of WGA-PEG to adsorb to dehydrated mucins and restore the hydration to the level of native mucins. The dehydrated monolayer was obtained by chemical de-glycosylation of the mucin. The de-glycosylated mucins are designated as "pApoPGM" in the graph. The control lectin-PEG conjugate is (pApoPGM+SNA-PEG). The *Sambucus Nigra* lectin (SNA), which specifically binds sialic acid residues, was conjugated to PEG. The mucins used here are poor in sialic acid and allow only little binding of the conjugate to the layer and thus to minimal re-hydration. This control excludes any non-specific binding of the conjugate to the surface under the mucin layer.

Partially deglycosylated coatings approximating an altered mucus layer was subjected to WGA-PEG (see FIG. 7). The WGA-PEG conjugate successfully bound the partially deglycosylated mucin and restored the hydration to the level of native mucins. Importantly, a control Lectin-PEG conjugate that binds minimally to PGM, did not restore hydration, thus excluding any effect of non-specific adsorption. The conjugate as thus preserved both the sugar binding ability of WGA and the high hydration of PEG.

WGA-PEG Acts as an Antifouling Coating for Biological Surfaces

Figures 8A, 8B:
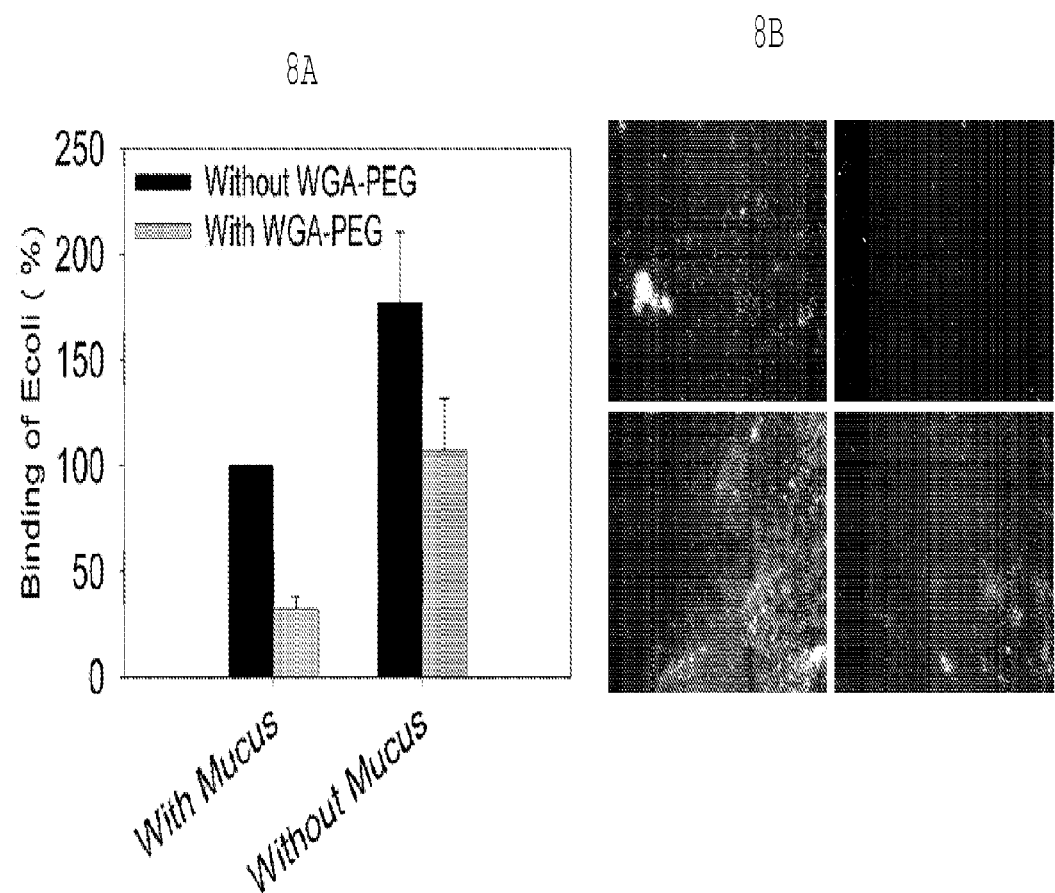
FIGS. 8A-8B show the capacity of WGA-PEG that is bound to cells or the mucus layer covering cells, to decrease binding of *E. coli*. 8A is a bar graph showing that the addition of WGA-PEG to HT29-MTX cells reduced the adhesion of *E. coli*, both in the presence of mucus, and after treatment of the cell line with the mucolytic N-acetylcysteine (NAC). 8B images show GFP-expressing bacteria on the cell surface as follows: Top-left—Cell without WGA-PEG; Top-right—Cells treated with WGA-PEG; Bottom-left—Cells treated with NAC without WGA-PEG; Bottom-right—Cells treated with NAC then with WGA-PEG.

One important role of mucus is it ability of preventing infection from pathogen. The mucosa achieves this in several ways, including by a constant turnover of mucus and the secretion of antimicrobial peptides. Here, we aim at replicating one aspect of this defense system: the ability to preventing attachment of bacteria to the surface of the epithelium. A large body of work has studied the deposition of PEG or pegylated polymer synthetic surfaces to form effective antifouling coatings, however this has not been applied to biological surfaces in a significant fashion. With the goal of creating an antifouling surface modification for the mucosa, we tested the ability of WGA-PEG to prevent GFP-expressing *E. coli* from adhering to the surface of the mucus-producing HT29-MTX epithelial cells. As seen in FIG. 8, the addition of WGA-PEG to the cells decrease bacteria attachment to the biological surface, both when mucus was present or not. Repelling bacteria might be very interesting in the case of mucosa is injured and vulnerable because imperfect mucus coverage.

WGA-PEG is not Toxic to Cells, Bacteria and Zebra Fish Embryos

Figures 9A, 9B, 9C, 9D:
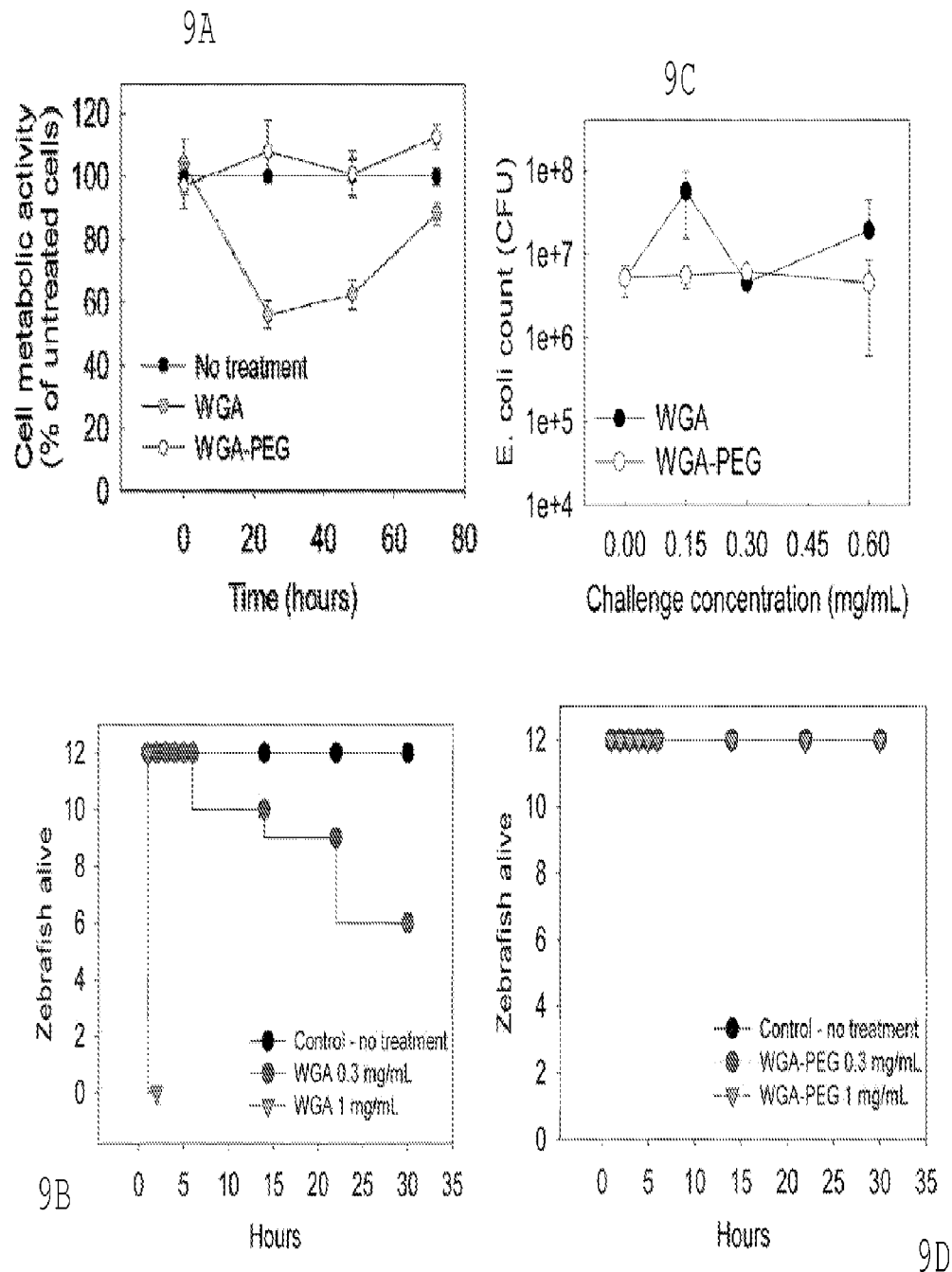
FIGS. 9A-9D show the toxicity of WGA and WGA-PEG on bacteria, the HT29-MTX cells, and on zebra fish embryos. In 9A. WGA or WGA-PEG was exposed at 0.3 mg/mL to the mucus-producing epithelial cell line HT29-MTX for 1 hour. Metabolic activity, measured through the change of fluorescence of the "Alamar Blue" dye, is correlated with viability of the cells. No decrease in metabolic activity was measured for WGA-PEG treated cells. While WGA-treated cells saw a decrease over the first couple of days. 9C provides *E. coli* colony-counts for bacteria (*E. coli*) after treatment for 1 hour with either WGA or WGA-PEG at different concentrations. The CFU where about the same with or without WGA or WGA-PEG treatments. In 9B and 9D, the graphs represent the number of live zebra fish embryo. Here either WGA or WGA-Peg was left in the water of the fish for up to 30 hours. WGA-treated fish died within the 30 hours while control and WGA-PEG exposed-fish did not.

Although lectins are part of our daily diet and a natural part of our mucus, some have been shown to be toxic to cells. The potential toxicity of the conjugate can be problematic to several respects. First, the molecules can be toxic to epithelial cells and induces undesired inflammation. As shown in FIG. 9A, the effect of WGA-PEG on the cells was assessed by measuring their metabolic activity after a 1 hour exposure. Although WGA showed some toxicity in the first 24 hours, no effect could be seen for WGA-PEG. Second, the mucosa is also the host of trillions of microbes forming our microbiome. Although a temporary repulsion of incoming bacteria might be effective at preventing infections, a generalize toxicity to bacteria could disturb the delicate microbiome which can have severe pathological consequence. FIG. 9C shows colony-counts (CFU) for WGA-PEG exposed *E. coli*, revealing that there is no toxicity of the conjugate or WGA at the concentration used here. Finally, we evaluated the systematic toxicity of the conjugate by exposing it to zebra fish embryos over 30 hours. Zebra fish are increasingly being used as model organisms for screening of new drugs since they are obtained easily, highly sensitive to toxic molecules and transparent. No fish died from the exposure to WGA-PEG, however WGA did show high toxicity, especially at 1 mg/mL (FIG. 9B, 9D). We hypothesis that the presence of the large PEG molecules on the lectin can alter the ability to enter cells, which has been linked to cell toxicity.

```
SEQ ID NO: 1:
  1    qrcgeqgsgm ecpnnlccsq ygycgmggdy cgkgcqngac
       wtskrcgsqa ggktcpnnhc
```

```
61      csqyghcgfg aeycgagcqg gpcradikcg sqaggklcpn
        nlccsqwgyc glgsefcgeg 121     cqngacstdk pcgKdaggrv ctnnyccskw gscgigpgyc
        gagcqsggcd gvfaeaiatn 181     stllae //
```

It should be understood that for all numerical bounds describing some parameter in this application, such as "about," "at least," "less than," and "more than," the description also necessarily encompasses any range bounded by the recited values. Accordingly, for example, the description at least 1, 2, 3, 4, or 5 also describes, inter alia, the ranges 1-2, 1-3, 1-4, 1-5, 2-3, 2-4, 2-5, 3-4, 3-5, and 4-5, et cetera.

For all patents, applications, or other reference cited herein, such as non-patent literature and reference sequence information, it should be understood that it is incorporated by reference in its entirety for all purposes as well as for the proposition that is recited. Where any conflict exits between a document incorporated by reference and the present application, this application will control. All information associated with reference gene sequences or protein domains disclosed in this application, such as GeneIDs or accession numbers (typically referencing NCBI accession numbers), including, for example, genomic loci, genomic sequences, functional annotations, allelic variants, and reference mRNA (including, e.g., exon boundaries or response elements) and protein sequences (such as conserved domain structures) are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g. elements, including numerical ranges and exemplary embodiments) of particular embodiments and aspects of the invention including the working examples. For example, particular experimental parameters exemplified in the working examples can be adapted for use in the claimed invention piecemeal without departing from the invention. For example, for material is that are disclosed, while specific reference of each various individual and collective combinations and permutation of these compounds may not be explicitly disclosed, each is specifically contemplated and described herein. Thus, if a class of elements A, B, and C are disclosed as well as a class of elements D, E, and F and an example of a combination of elements, A-D is disclosed, then even if each is not individually recited, each is individually and collectively contemplated. Thus, is this example, each of the combinations A-E, A-F, B-D, B-E, B-F, C-D, C-E, and C—F are specifically contemplated and should be considered disclosed from disclosure of A, B, and C; D, E, and F; and the example combination A-D. Likewise, any subset or combination of these is also specifically contemplated and disclosed. Thus, for example, the subgroup of A-E, B-F, and C-E are specifically contemplated and should be considered disclosed from disclosure of A, B, and C; D, E, and F; and the example combination A-D. This concept applies to all aspects of this application including, elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art—thus to the extent an element is described in one or more references known to the person having ordinary skill in the art, they may be excluded from the claimed invention by, inter alia, a negative proviso or disclaimer of the feature or combination of features.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating dehydration of a mucosal surface of a human in need thereof, comprising contacting the mucosal surface with an effective amount of a composition that includes a conjugate of a hydratable polymer and a mucin-binding fragment of a lectin, thereby rehydrating the mucosal surface of the human.

2. The method of claim 1, wherein the mucosal surface is the mucosal surface of the eyes, mouth, nose, female genital tract, respiratory tract, or digestive tract.

3. The method of claim 1, wherein the hydratable polymer is hydrated.

4. The method of claim 1, wherein the hydratable polymer is a polyether.

5. The method of claim 4, wherein the polyether is a polyethylene glycol.

6. The method of claim 5, wherein the polyethylene glycol has an average molecular weight of at least 10, 20, 30, 40, 50, 60, 70 or 80 Kda.

7. The method of claim 1, wherein the mucin-binding fragment of the lectin includes a fragment of a wheat germ agglutinin lectin.

* * * * *

SEQUENCE LISTING

```
<160> NUMBER OF SEQ ID NOS: 1

<210> SEQ ID NO 1
<211> LENGTH: 186
<212> TYPE: PRT
<213> ORGANISM: Triticum aestivum (Wheat)

<400> SEQUENCE: 1

Gln Arg Cys Gly Glu Gln Gly Ser Gly Met Glu Cys Pro Asn Asn Leu
  1               5                  10                  15

Cys Cys Ser Gln Tyr Gly Tyr Cys Gly Met Gly Gly Asp Tyr Cys Gly
             20                  25                  30

Lys Gly Cys Gln Asn Gly Ala Cys Trp Thr Ser Lys Arg Cys Gly Ser
         35                  40                  45

Gln Ala Gly Gly Lys Thr Cys Pro Asn Asn His Cys Cys Ser Gln Tyr
     50                  55                  60

Gly His Cys Gly Phe Gly Ala Glu Tyr Cys Gly Ala Gly Cys Gln Gly
 65                  70                  75                  80

Gly Pro Cys Arg Ala Asp Ile Lys Cys Gly Ser Gln Ala Gly Gly Lys
                 85                  90                  95
```

```
Leu Cys Pro Asn Asn Leu Cys Cys Ser Gln Trp Gly Tyr Cys Gly Leu
            100                 105                 110

Gly Ser Glu Phe Cys Gly Glu Gly Cys Gln Asn Gly Ala Cys Ser Thr
        115                 120                 125

Asp Lys Pro Cys Gly Lys Asp Ala Gly Gly Arg Val Cys Thr Asn Asn
        130                 135                 140

Tyr Cys Cys Ser Lys Trp Gly Ser Cys Gly Ile Gly Pro Gly Tyr Cys
145                 150                 155                 160

Gly Ala Gly Cys Gln Ser Gly Gly Cys Asp Gly Val Phe Ala Glu Ala
                165                 170                 175

Ile Ala Thr Asn Ser Thr Leu Leu Ala Glu
            180                 185
```